(12) United States Patent
Tachikawa et al.

(10) Patent No.: US 7,111,848 B2
(45) Date of Patent: Sep. 26, 2006

(54) GASKET AND METHOD OF MANUFACTURING THE GASKET

(75) Inventors: Kouichi Tachikawa, Yamanashi (JP); Hiroyuki Yunoki, Yamanashi (JP); Yutaka Kikuchi, Saitama (JP)

(73) Assignees: Terumo Kabushiki Kaisha, Tokyo (JP); Kokoku Intech Co., Ltd., Tokyo (JP)

( * ) Notice: Subject to any disclaimer, the term of this patent is extended or adjusted under 35 U.S.C. 154(b) by 314 days.

(21) Appl. No.: 10/380,518

(22) PCT Filed: Sep. 14, 2001

(86) PCT No.: PCT/JP01/08014

§ 371 (c)(1),
(2), (4) Date: Mar. 14, 2003

(87) PCT Pub. No.: WO02/22192

PCT Pub. Date: Mar. 21, 2002

(65) Prior Publication Data

US 2004/0084852 A1 May 6, 2004

(30) Foreign Application Priority Data

Sep. 14, 2000 (JP) .................................... 2000-280913
Sep. 14, 2000 (JP) .................................... 2000-280914

(51) Int. Cl.
*A61M 5/315* (2006.01)
*F16J 15/20* (2006.01)

(52) U.S. Cl. ........................................ 277/535; 604/230
(58) Field of Classification Search ......... 526/247–255; 428/35.2–35.7, 66.4, 492–494, 141, 421; 106/36; 277/534, 535, 538; 604/230, 218
See application file for complete search history.

(56) References Cited

U.S. PATENT DOCUMENTS

| | | | | |
|---|---|---|---|---|
| 4,303,070 A | * | 12/1981 | Ichikawa et al. | 604/222 |
| 4,997,423 A | * | 3/1991 | Okuda et al. | 604/230 |
| 5,009,646 A | * | 4/1991 | Sudo et al. | 604/230 |
| 5,061,247 A | * | 10/1991 | Akaike et al. | 604/187 |
| 5,549,573 A | * | 8/1996 | Waskonig | 604/218 |
| 6,090,081 A | * | 7/2000 | Sudo et al. | 604/230 |
| 6,093,175 A | * | 7/2000 | Gyure et al. | 604/230 |
| 6,150,035 A | * | 11/2000 | DeFife et al. | 428/500 |

FOREIGN PATENT DOCUMENTS

| | | | |
|---|---|---|---|
| EP | 0879611 A2 | * | 11/1998 |
| EP | 0 879 611 A2 | | 11/1998 |
| JP | 6-66689 U | | 9/1994 |
| JP | 666689 U | * | 9/1994 |

* cited by examiner

*Primary Examiner*—Nicholas D. Lucchesi
*Assistant Examiner*—Sundeep S Virdi
(74) *Attorney, Agent, or Firm*—Burns, Doane, Swecker & Mathis, LLP

(57) ABSTRACT

A gasket is capable of providing an excellent slidabiity and holding its sealability without applying lubricant and a gasket that can prevent a resin film from being peeled off of a gasket body and prevent the generation of a molding defect such as pinholes. The gasket can be installed slidably in a outer tube of a syringe, including a gasket body and a resin film formed of a material lower in coefficient of friction than a material of the gasket body, which covers at least an outer periphery of the gasket body, in which when a surface roughness of the resin film on the outer tube side is defined as $Ra_1$ and a surface roughness of the resin film on the gasket body side is defined as $Ra_2$, a relationship of $1.5\ Ra_1 \leq Ra_2$ is satisfied.

10 Claims, 3 Drawing Sheets

GASKET AND METHOD OF MANUFACTURING THE GASKET

TECHNICAL FIELD

The present invention relates to a gasket and a method of manufacturing the same.

BACKGROUND ART

In general, a syringe is composed of an outer tube, a gasket slidable in the outer tube, and a plunger for moving the gasket.

Conventionally, furthermore, for example, a gasket made of an elastic material such as vulcanized rubber or thermoplastic elastomer has been widely used.

Such a gasket has a large sliding resistance between the gasket and the inner peripheral surface of the outer tube, so that lubricant has been applied on the surface of the gasket or the inner peripheral surface of the outer tube to decrease the sliding resistance between the gasket and the inner peripheral surface of the outer tube.

However, such a syringe has the following problems, for example, when a drug solution or the like is contained in the outer tube.

(1) There is a possibility that in the drug solution contained in the outer tube, the lubricant applied on the surface of the gasket or the inner peripheral surface of the outer tube is mixed, which may affect the medicinal ingredients of the drug solution.

(2) There is a possibility that the medicinal ingredients of the drug solution contained in the outer tube are adsorbed (bonded) to the lubricant applied onto the surface of the gasket or the inner peripheral surface of the outer tube.

For solving the conventional problems described above, it is conceivable that a gasket is composed of a gasket body and a film covering at least the outer periphery of the gasket body in which the film is formed of a material having a friction resistance smaller than the material of the gasket body to omit the application of lubricant on the surface of the gasket.

In this kind of the gasket, however, depending on the surface qualities (conditions) of the film or the material of the film, there is a possibility that the film is peeled off of the gasket body or sealability and slidability with respect to the inner peripheral surface of the outer tube of the syringe decrease. Furthermore, depending on the thickness of the film, there is a possibility of causing a molding defect such as pinholes.

The inventors of the present invention have found out that these disadvantages could be solved by properly selecting the surface qualities of both surfaces of the resin film for covering the gasket body, and material and thickness of the resin film, and thus the gasket of the present invention has been finally completed.

Furthermore, in the gasket described above, there is a possibility that a step of preparing a film or a step of coating a gasket body with the film is complicated. In these steps, there is a possibility of causing a molding defect such as pinholes.

The inventors of the present invention have found out that these disadvantages could be solved by properly selecting the method of preparing a resin film and the method of coating the gasket body with the resin film, and thus the method of manufacturing the gasket of the present invention has been finally completed.

DISCLOSURE OF THE INVENTION

A first object of the present invention is to provide a gasket capable of providing an excellent slidability and holding its sealability without applying lubricant, and furthermore to provide a gasket that can prevent a resin film from being peeled off of a gasket body and prevent the generation of a molding defect such as pinholes.

The object can be attained according to the following items (1) to (10) of the present invention.

(1) A gasket installed slidably in an outer tube of a syringe, including a gasket body and a resin film formed of a material lower in coefficient of friction than a material of the gasket body, which covers at least an outer periphery of the gasket body, in which when a surface roughness of the resin film on the outer tube side is defined as $Ra_1$ and a surface roughness of the resin film on the gasket body side is defined as $Ra_2$, a relationship of $1.5\, Ra_1 \leq Ra_2$ is satisfied.

(2) The gasket as described in the item (1), in which the surface roughness $Ra_1$ is 0.1 to 1.5 μm.

(3) The gasket as described in the item (1) or (2), in which $Ra_2 < 0.5T$ when an average thickness of the resin film is defined as T.

(4) The gasket as described in the item (3), in which the average thickness T of the resin film is 1 to 200 μm.

(5) The gasket as described in any one of the items (1) to (4), in which the surface of the resin film on the outer tube side has a coefficient of kinetic friction (against a sapphire needle) of 0.3 or less.

(6) The gasket described in any one of the items (1) to (5), in which the resin film is formed of a fluorocarbon resin.

(7) The gasket as described in any one of the items (1) to (6), in which the surface roughness $Ra_2$ is adjusted by subjecting the surface of the resin film on the gasket body side to a surface roughening.

(8) The gasket as described in the item (7), in which the surface roughening is performed by using an etching process.

(9) The gasket as described in any one of the items (1) to (8), in which the gasket body and the resin film are put into close contact with each other such that the gasket material enters into a plurality of minute recessed portions of the surface of the resin film on the gasket body side.

(10) The gasket as described in any one of the items (1) to (9), in which the gasket body is formed of an elastic material.

In addition, a second object of the present invention is to provide a method of manufacturing a gasket, which makes it possible to obtain a gasket by a simple manufacturing step by which the generation of a molding defect such as pinholes can be prevented.

This object can be attained according to the following items (11) to (23) of the present invention.

(11) A method of manufacturing a gasket by covering an outer periphery of a gasket body with a resin film manufactured by a skiving processing to obtain a gasket including: placing the resin film and a gasket body material formed of a material capable of obtaining an elasticity by vulcanization in a molding die; performing heating and pressurizing to vulcanize the material capable of obtaining the elasticity by the vulcanization; and coating the resin film on an outer peripheral surface of the gasket body to obtain the gasket.

(12) The method of manufacturing a gasket as described in the item (11), in which the heating is performed at a temperature of 140 to 180° C.

(13) The method of manufacturing a gasket as described in the item (11) or (12), in which the pressurizing is performed at a pressure of 0.5 to 25 MPa.

(14) The method of manufacturing a gasket as described in any one of the items (11) to (13), in which a surface roughening is performed on a surface of the resin film on the gasket body side prior to molding.

(15) The method of manufacturing a gasket as described in the item (14), in which the surface roughening is one performed by an etching process.

(16) The method of manufacturing a gasket as described in the item (14) or (15), in which the surface of the resin film on the gasket body side satisfies a relation of a coefficient of kinetic friction ratio $F=D_2/D_1 \geqq 2$ when a coefficient of kinetic friction (against a sapphire needle) before the surface roughening is defined as $D_1$ and a coefficient of kinetic friction (against a sapphire needle) after the surface roughening is defined as $D_2$.

(17) The method of manufacturing a gasket as described in any one of the items (11) to (16), in which the surface of the resin film on the gasket body side satisfies the relation in which $Ra_4/Ra_3$ is 0.25 to 0.9 when a surface roughness before molding is defined as $Ra_3$ and a surface roughness after molding is defined as $Ra_4$.

(18) The method of manufacturing a gasket as described in the item (17), in which the surface roughness $Ra_4$ is 0.1 to 1.5 μm.

(19) The method of manufacturing a gasket as described in any one of the items (11) to (18), in which a surface of the resin film opposite to the gasket body side has a coefficient of kinetic friction (against a sapphire needle) after molding of 0.3 or less.

(20) The method of manufacturing a gasket as described in any one of the items (11) to (19), in which an average thickness $T_1$ of the resin film before molding is 25 μm or more.

(21) The method of manufacturing a gasket as described in any one of the items (11) to (20), in which an average thickness $T_2$ of the resin film after molding is 1 to 200 μm.

(22) The method of manufacturing a gasket as described in any one of the items (11) to (21), in which the resign film is covered with the gasket body such that the gasket material enters into a plurality of minute recessed portions of the surface of the resin film on the gasket body side.

(23) The method of manufacturing a gasket as described in any one of the items (11) to (22), in which the resin film is formed of a material lower in coefficient of friction than the gasket body material.

BEST MODE FOR CARRYING OUT THE INVENTION

Hereinafter, the gasket of the present invention and the method of manufacturing a gasket of the present invention will be described in detail on the basis of preferred embodiments shown in the attached drawings.

At first, the gasket of the present invention will be described with reference to FIG. 1.

Figure 1:
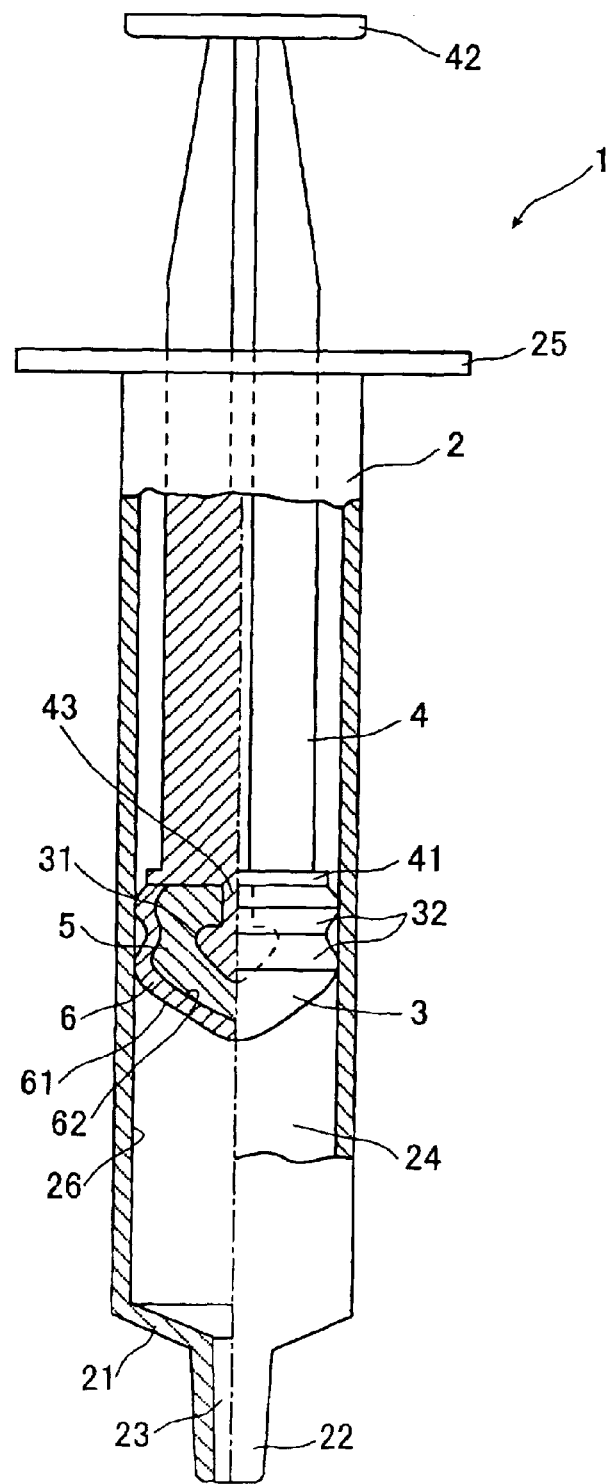
FIG. 1 is a partial vertical cross sectional view showing a configuration of a syringe having the gasket of the present invention.

FIG. 1 is a partial vertical cross sectional view showing a configuration of a syringe having the gasket of the present invention. In the following description, an upper side in FIG. 1 is referred to as "a base end" and a lower side thereof is referred to as "a tip end".

The syringe 1 shown in FIG. 1 includes an outer tube 2, a gasket 3 slidable in the outer tube 2, and a plunger 4 attached to the gasket 3 and for moving the gasket 3. Hereinafter, the configuration of each part will be described.

The outer tube 2 is constructed of a closed-end cylindrical member having a bottom part 21. In the center region of the bottom part 21, a diameter reduction part 22 having a diameter reduced from that of the body part of the outer tube 2 is integrally formed. This diameter reduction part 22 is used by fitting in and attaching to a hub of a needle tube such as one for the administration of a drug solution or drawing blood; a wide variety of connectors; a tube; a catheter; or the like (not shown).

In this outer tube 2, a containment space 24 is formed in the portion enclosed with the gasket 3 described below and the outer tube 2, and the containment space 24 is communicated with an inner cavity 23 of the diameter reduction part 22.

In the containment space 24, for example, blood, carbohydrate injections such as glucose; electrolyte compensation injections such as sodium chloride and potassium lactate; various drug solutions; vitamin compounds, vaccines, antibiotic injections, contrast media, steroids, endopeptidase inhibitors, fat emulsions, anticancer agents, anesthetics, stimulants, and narcotics; and liquids such as distilled water, disinfectant, fluid food, and alcohol can be contained.

Furthermore, a plate-shaped flange 25 is integrally formed on the outer periphery of the base end of the outer tube 2. Upon moving the plunger 4 relative to the outer tube 2, the operation can be performed by having fingers caught in the flange 25.

The outer tube 2 is preferably formed of a clear (colorless and transparent), colored and transparent, or translucent resin, so that the visibility of the containment space 24 is ensured.

As to a constitution material of the outer tube 2, although not specifically limited, there can be employed polyesters such as polyethylene terephthalate and polyethylene terephthalate copolymer; acrylic resins such as polyacrylonitril, polymethyl methacrylate, and polymethacrylic acid; polyolefin such as polypropylene and polyethylene; polyvinyl chloride; polyamide such as nylon; thermoplastic resins such as polystyrene, polyethylene naphthalate, cyclic polyolefin (e.g., copolymer of ethylene and tetracyclo[$4.4.0.1^{2.5}.1^{7.10}$]-3-dodecene), polymethyl pentene, polycarbonate, and polysulfone.

Using such a thermoplastic resin, it is advantageous in terms of a reduction in the production cost, weight reduction, and an expansion of the range of selecting the shapes of the outer tube 2, in addition, the resistance to breakage of the outer tube 2 is improved.

In the outer tube 2, the gasket 3 is housed (arranged). This gasket 3 has an impacting part (a hollow portion) 31, and a head portion 43 of the plunger 4 described below is fit into the impacting part 31.

The gasket 3 is constructed of a substantially cylindrical member and the outer periphery part thereof has a pair of ring-shaped protruded portions 32 extending toward the inner peripheral surface 26 of the other tube 2 and being spaced at a certain distance in the longitudinal direction. These protruded portions 32 are slid on the inner peripheral surface 26 of the outer tube 2 while keeping in absolute contact therewith, so that it can be possible to retain the sealability more reliably and to achieve an improvement of the slidability.

In addition, the details of the gasket 3 of the present invention will be described later.

This kind of gasket 3 is coupled with the plunger 4 that moves the gasket 3 along the inside of the outer tube 2 in the longitudinal direction.

The plunger 4 is principally constructed of a member having a cross-shaped lateral cross section and a plate member 41 is integrally formed on the tip side thereof. In addition, a plate-shaped (disk-shaped) flange 42 is integrally formed on the base end of the plunger 4. The plunger 4 is operated by having fingers or the like caught in the flange 42.

In addition, on the tip end portion of the plunger 4, there is formed a mushroom-shaped head part (a coupling part) 43 to be inserted and fit in the impacting part 31 of the gasket 3.

Note that, instead of the fitting, a fixing method of the plunger 4 to the gasket 3 may be, for example, a method of calking, fusion bonding, adhesion with an adhesive, or screwing.

The materials for constituting the plunger 4 include various kinds of resins such as polyvinylchloride, polyethylene, polypropylene, polystyrene, poly-(4methylpentene-1), polycarbonate, acryl resin, acrylonitrile-butadiene-styrene copolymer, polyesters such as polyethylene terephthalate, butadiene-styrene copolymer, and polyamide (e.g., nylon 6, nylon 6-6, nylon 6-10, and nylon 12). Among them, resins such as polypropylene, polyester, and poly-(4-methylpentene-1) are preferable in terms of easy molding.

The present invention is characterized in the configuration of the gasket 3. Hereinafter, the gasket 3 will be described in detail.

The gasket 3 of the present embodiment is composed of a gasket body 5 and a resin film 6 that covers the outer surface of the gasket body 5.

The gasket body 5 is one functioning as a core part (a core member) of the gasket 3 and is formed of an elastic material.

When the gasket body 5 is formed of the elastic material and the maximum outer diameter of the gasket 3 is set to one slightly larger than the inner diameter of the outer tube 2, the outer periphery of the gasket 3 is brought into press-contact with the inner peripheral surface 26 of the outer tube 2 due to the elastic force of the gasket body 5 to improve sealability.

As to such an elastic material, although not specifically limited, there can be employed one or a combination of two or more selected from various kinds of rubber materials such as natural rubber, butyl rubber, isoprene rubber, butadiene rubber, styrene-butadiene rubber, and silicone rubber, various kinds of thermoplastic elastomers such as polyurethane type, polyester type, polyamide type, olefin type, and styrene type, and so forth.

Among them, in the case of applying the method of manufacturing a gasket of the present invention described below, a material by which the elasticity can be obtained by vulcanization is used. The use of such a material and the application of the method of manufacturing a gasket of the present invention described below allow the vulcanization of the material of the gasket body under heat and pressure at the time of molding the gasket 3, so that an additional step of vulcanizing the material of the gasket body can be omitted, which is advantageous in reduce of manufacturing costs and manufacturing time for the gasket 3.

In the present embodiment, the outer surface of the gasket body 5 (except for a region of the gasket body 5 abutting against the plate member 41 of the plunger 4) is covered with a resin film 6 made of a material having a smaller coefficient of friction than the above elastic material (the constitution material of the gasket body 5).

If the gasket body is not covered with the resin film, i.e., if the gasket is formed of an elastic material such as a vulcanized rubber or a thermoplastic elastomer, the outer periphery of the gasket showed an extremely large sliding resistance to the inner peripheral surface 26 of the outer tube 2. Therefore, in such a gasket, there is a need of reducing the sliding resistance between the outer periphery of the gasket and the inner peripheral surface 26 of the outer tube 2 by applying lubricant on the outer surface (outer periphery) thereof or the inner peripheral surface 26 of the outer tube 2. Therefore, in a syringe having this gasket, when a drug solution or the like is contained in the containment space 24 of the outer tube 2, for example, the above lubricant may be mixed (dissolved) in the drug solution and the lubricant may act on (react with) the medicinal ingredients of the drug solution to cause a decrease in the activity. In addition, the medicinal ingredients in the drug solution contained in the containment space 24 may be adsorbed (bonded) to the above lubricant and the concentrations of the medicinal ingredients in the drug solution may decrease, so that sufficient quantities of the medicinal ingredients may be hardly supplied.

On the contrary, in the gasket 3 of the present invention, as the gasket body 5 is covered with the resin film 6, the sliding resistance between the outer periphery of the gasket 3 and the inner peripheral surface 26 of the outer tube 2 can be reduced. Accordingly, there is no need to apply lubricant on the outer surface (the outer surface 61 of the resin film 6) of the gasket 3 or the inner peripheral surface 26 of the outer tube 2 (alternatively, only applying the lubricant in a smaller amount than the conventional one). For instance, the activities and concentrations of medicinal ingredients in the drug solution can be prevented from decreasing even though the drug solution or the like is contained in the containment space 24 of the outer tube 2.

When attention is paid to the slidability of the gasket 3, the coefficient of kinetic friction (against a sapphire needle) of the outer surface (the surface toward the outer tube 2 side) 61 of the resin film 6 is preferably about 0.3 or less, more preferably about 0.1 to 0.2.

Furthermore, a high sealability is also required for the outer surface 61 of the resin film 6 in addition to a high slidability to the inner peripheral surface 26 of the outer tube 2.

When the surface roughness (a center line mean roughness defined in JIS B 0601) $Ra_1$ of the outer surface 61 is too small, the contact area with the inner peripheral surface 26 of the outer tube 2 increases and then the sliding resistance to the inner peripheral surface 26 increases. Therefore, in terms of an improvement in the slidability, it is preferable that the surface roughness $Ra_1$ of the outer surface 61 is larger. However, when the surface roughness $Ra_1$ of the outer surface 61 is too large, the contact area with the inner peripheral surface 26 of the outer tube 2 becomes small, causing a decrease in the sealability with the inner peripheral surface 26 of the outer surface 61. Therefore, in terms of an improvement in the sealability, a smaller surface roughness $Ra_1$ of the outer surface 61 is preferable. That is, a high slidability and a high sealability to the inner peripheral surface 26 of the outer tube 2, which are required for the outer surface 61, are ambivalent characteristics.

Therefore, in terms of compatibility between a high slidability and a high sealability of the outer surface 61 to the inner peripheral surface 26 of the outer tube 2, there is a preferable range of the surface roughness $Ra_1$ of the outer surface 61. Such a range is preferably about 0.1 to 1.5 μm, more preferably of about 0.25 to 0.8 μm.

On the other hand, there is no demand to provide the inner surface (the surface toward the gasket body 5 side) 62 of the resin film 6 with slidability and sealability, while there is a demand to provide the outer surface of the gasket body 5 with a high adhesiveness.

Therefore, the surface roughness $Ra_2$ of the inner surface 62 (a center line mean roughness defined in JIS B 0601) is defined such that it is larger than the surface roughness $Ra_1$ of the outer surface 61. Specifically, it is one filling the relation of $1.5Ra_1 \leq Ra_2$, preferably one filling the relation of $1.8Ra_1 < Ra_2$, more preferably one filling the relation of $3.0Ra_1 < Ra_2$.

When the surface roughness $Ra_2$ of the inner surface 62 is smaller than the above lower limit, the contact area between the inner surface 62 and the outer surface of the gasket body 5 becomes small and then the adhesiveness of the inner surface 62 to the outer surface of the gasket body 5 decreases to peel the resin film 6 out of the gasket body 5.

Furthermore, although the upper limit of the surface roughness $Ra_2$ of the inner surface 62 is not limited, it is for example preferably $Ra_2<0.5T$ in relation to an average thickness T of the resin film 6 described later, more preferably $Ra_2<0.3T$, further preferably $Ra_2<0.1T$.

The thickness of the resin film 6 is prevented from becoming uneven by limiting the surface roughness $Ra_2$ of the inner surface 62 within the above range, so that the strength of the resin film 6 can be also retained properly.

The surface roughness $Ra_2$ of the inner surface 62 can be adjusted by subjecting the inner surface 62 of the resin film 6 to a surface roughening such as an etching process, a sand blasting process, or a shot blasting process. Among them, it is more preferable to perform the surface roughening with the etching process.

The average thickness T of the resin film 6 is, although not specifically limited, preferably about 1 to 200 μm, more preferably 15 to 110 μm. When the average thickness T of the resin film 6 is less than the above lower limit, there is a fear of becoming an insufficient strength. On the other hand, when the average thickness T of the resin film 6 exceeds the above upper limit, depending on the constitution material thereof, the sealability may decrease at the time of a deformation of the gasket 3 as the follow-up ability of the resin film 6 to the gasket body 5 decreases.

Note that, in FIG. 1, the thickness of the resin film 6 is illustrated in an exaggerated form for facilitating the understanding.

As to the constitution material of the resin film 6, although not specifically limited, there can be employed one or a combination of two or more fluorocarbon resins such as polytetrafluoroethylene or a copolymer thereof, an ethylene-tetrafluoroethylene copolymer, ethylene tetrafluoride-perfluoroalkoxy ethylene copolymer (e.g., a copolymer of ethylene tetrafluoride and perfluoroalkoxy ethylene having a carbon number of alkoxy group of 1 to 5), PVDF (polyfluoro vinylidene)-HFP (hexafluoropropylene) copolymer, PCTFE (polychlorotrifluoroethylene), and PTFE (polytetrafluoroethylene), FEP (tetrafluoroethylene-fluoropropylene copolymer).

In the gasket 3, furthermore, the gasket body 5 and the resin film 6 are kept in absolute contact with each other such that the material of the gasket body can be entered into a plurality of minute recessed portions of the inner surface 62 of the resin film 6. Accordingly, the adhesiveness between the resin film 6 and the gasket body 5 further increases, and also the resin film 6 can be prevented from being peeled off of the gasket body 5 more reliably when the gasket 3 slides in the outer tube 2, in particular even in the vicinity of the protruded portions 32 which are portions being facilitated to be peeled off as stress is concentrated thereon.

Note that, the gasket 3 is not limited to one configured as shown in the figure, and alternatively the resin film 6 may cover at least only the outer periphery of the gasket body 5. Furthermore, the shape thereof may be any shape as far as it has sufficient slidability and sealability to the inner peripheral surface 26 of the outer tube 2.

Such a kind of gasket 3 can be manufactured, for example, as follows.

<1> At first, a sheet (the resin film 6 before covering the gasket body 5) having predetermined dimensions and predetermined surface roughness (a center line mean roughness defined in JIS B 0601) is prepared. A method of manufacturing the sheet, although not specifically limited, may include skiving processing, casting, injection molding, and extrusion molding.

By adjusting the thickness and the surface roughness of the sheet, the surface roughness $Ra_1$ and the average thickness T of the outer surface 61 of the resin film 6 in the finished product are adjusted.

<2> The surface of the sheet to serve as an inner surface 62 is subjected to an etching process for performing a surface roughening.

For this etching process, for example, etching process using sodium compound or sputter etching process can be used.

Note that, in accordance with the concentration of this process solution and the number of processes, the surface roughness $Ra_2$ of the inner surface 62 of the resin film 6 in the finished product is adjusted.

<3> Next, together with a mixture comprised of the gasket body materials, the above sheet is placed in a previously-heated molding die, and is then molded, for example, preferably at a die temperature of about 130 to 200° C., preferably at a molding clamping pressure of about 0.5 to 25 MPa, and preferably for a processing time of about 1 to 20 minutes, to obtain the finished product of the gasket 3.

Note that, when the gasket material requires vulcanization, the vulcanization may be simultaneously performed in this step. Accordingly, it becomes possible to omit the step of vulcanization of the gasket body material, which is advantageous in a reduction in manufacturing costs and a shortening of manufacturing time of the gasket 3.

<4> Next, the molded product of the gasket 3 is pulled out of the molding die and is then cooled at room temperature, followed by cutting and removing undesired portions by a trimming die to obtain the finished product of the gasket 3.

After passing through the above steps, the gasket 3 is manufactured.

Note that the gasket 3 may be prepared by previously forming the gasket body 5 and the resin film 6 into or almost into their respective shapes in the finished product and assembling the gasket body 5 and the resin film 6 together. In this case, as a method of adhering (fixing) the gasket body 5 and the resin film 6, for example, fitting, fusion bonding (thermal fusion bonding, high frequency fusion bonding, or the like), adhesion with an adhesive, or the like can be used.

Furthermore, for the manufacture of the gasket of the present invention, the method of manufacturing a gasket of the present invention to be described below is preferably used.

In the above description, the gasket of the present invention has been described with respect to the embodiment illustrated in the figure. However, the present invention is not limited to this.

Next, the method of manufacturing a gasket of the present invention will be described with reference to FIG. 2 and FIG. 3.

An example of a syringe having a gasket to be manufactured by the method of manufacturing a gasket of the present invention may include a syringe having the gasket of the present invention shown in FIG. 1 described above.

In the gasket manufactured by the method of manufacturing a gasket of the present invention, it is preferable that the outer surface of the gasket body 5 (except for a region of the gasket body 5 abutting against the plate member 41 of the plunger 4) is covered with the resin film 6 formed of a material having a smaller coefficient of friction than the above elastic material (the constitution material of the gasket body 5). However, the relation between the coefficients of friction of the both is not limited to this.

Figure 2:
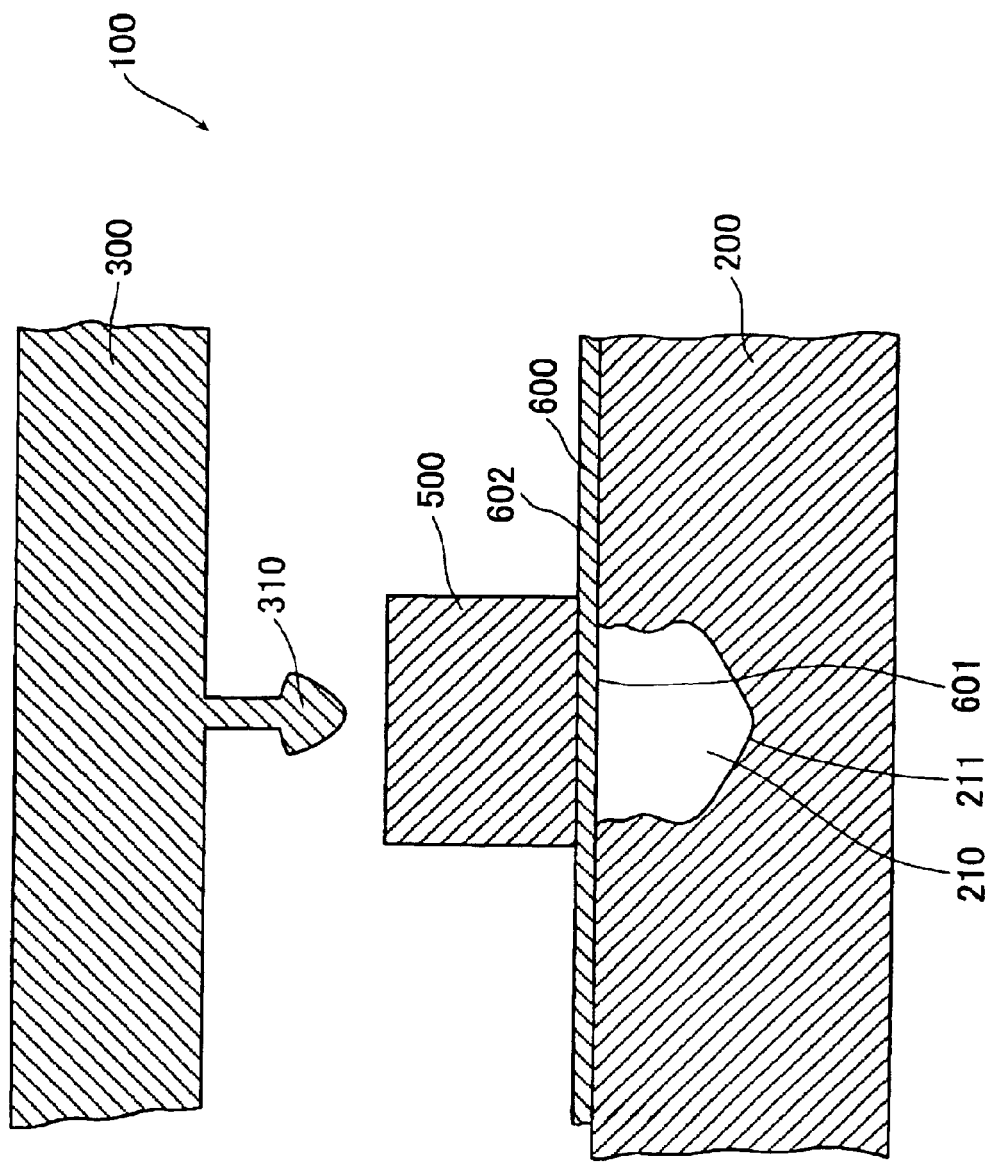
FIG. 2 is a diagram for illustrating the method of manufacturing a gasket of the present invention.
Figure 3:
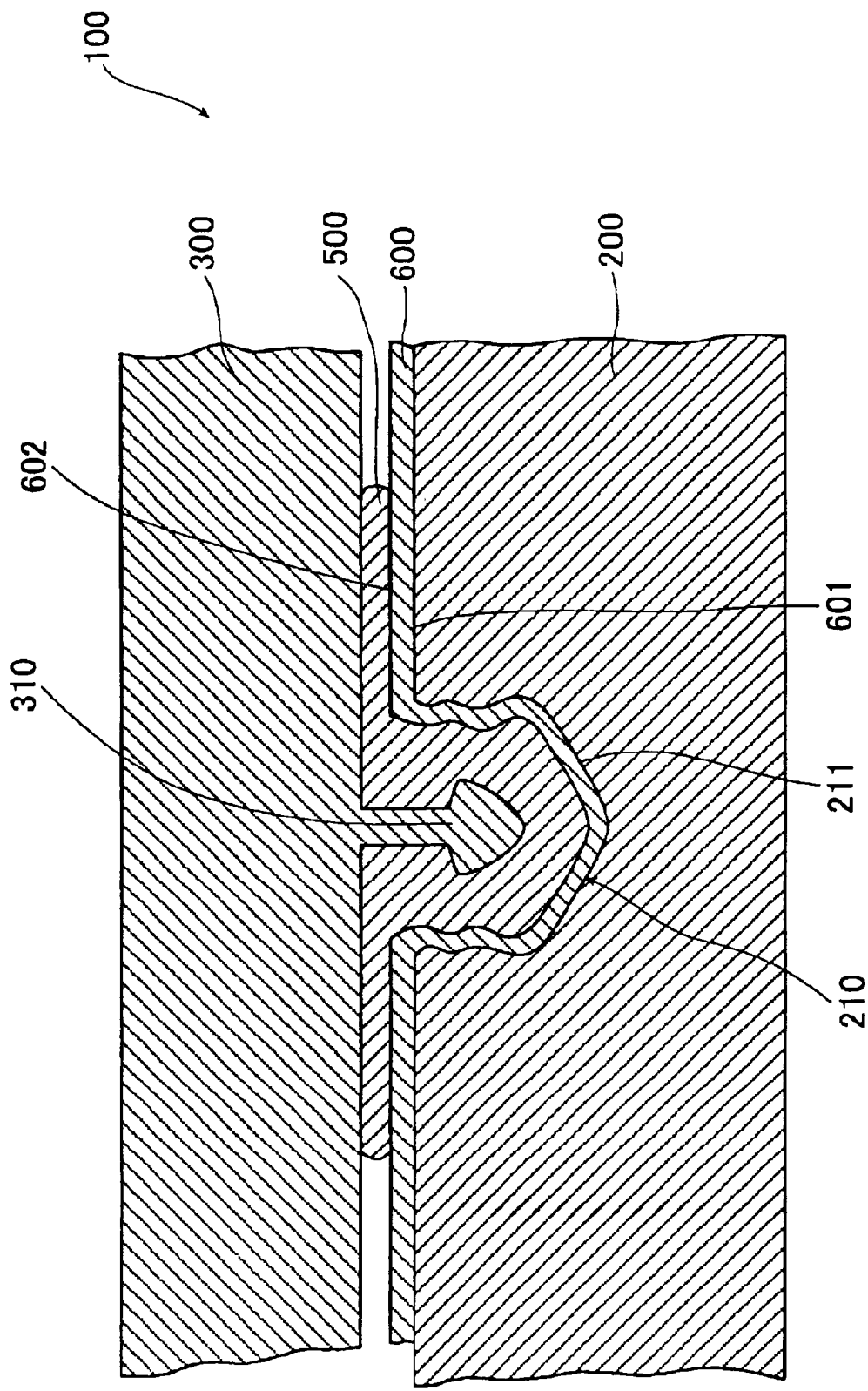
FIG. 3 is a diagram for illustrating the method of manufacturing a gasket of the present invention.

Each of FIG. 2 and FIG. 3 is a figure for illustrating the method of manufacturing a gasket of the present invention. Note that, in the following description, the resin film 6 before molding is referred to as a "sheet 600" and the resin film 6 after molding is referred to as a "resin film 6".

<1> At first, the sheet 600 is prepared.

In the method of manufacturing a gasket of the present invention, the sheet 600 is manufactured by a skiving processing. The reason of selecting the skiving processing as a method of manufacturing this sheet 600 will be described below.

For example, when a sheet is manufactured by a casting method, a relative thin sheet is only obtained. A sufficient strength cannot be obtained by the relative thin sheet. When such a sheet is applied in the method of manufacturing a gasket of the present invention, a molding defect such as pinholes may be generated at the time of molding the gasket as described below. In this case, furthermore, the step of manufacturing the sheet becomes complicated, so that there is a fear of causing an increase in manufacturing costs of the sheet and further an increase in manufacturing costs of the gasket.

On the contrary, when the sheet 600 is manufactured by the skiving processing, the relative thick sheet 600 can be easily and reliably manufactured. Therefore, the sheet 600 has a sufficient strength to thereby reliably prevent the generation of a molding defect such as pinholes at the time of molding the gasket 3.

Hereinafter, there is described a method of manufacturing the sheet 600 by the skiving processing.

At first, powder of the resin film material is filled in a bake molding die, and is then preformed by compressing preferably at about 0 to 30° C. under a pressure of 100 to 1000 kg/cm².

Next, the preformed product is baked (sintered) preferably at about 280 to 410° C., depending on the size of the preformed product, typically for 0.5 to 15 hours.

Next, a primary molded product formed of the resin film material is obtained by cooling at normal pressure or under pressure. The primary molded product is not limited to a specific shape and may be shaped like any form, for example a sheet, a block, or a cylinder.

Next, the primary molded product is placed on a lathe turning machine and is then rotated at a predetermined rotational frequency. While maintaining this state, a cutting blade is pressed against the primary molded product at a predetermined angle to cut, thereby obtaining the sheet 600.

Note that the average thickness $T_1$ of the sheet 600 and the surface roughness (a center line mean roughness defined in JIS B 0601) $Ra_3$ of the lower surface (the surface to serve as the outer surface 61 of the resin film 6) 601 are defined with consideration given to variations caused by the extension (the extension in the direction perpendicular to a thickness direction) of the sheet 600 at the time of molding described below.

Considering the variations caused by the extension of the sheet 600 at the time of molding, it is preferable to use one having an average thickness $T_1$ of about 25 μm or more, more preferably of about 40 to 80 μm, for example. On the other hand, although not specifically limited, the upper limit of the average thickness $T_1$ is suitably selected depending on the average thickness $T_2$ of the objective resin film 6.

In addition, the surface roughness $Ra_3$ is suitably selected depending on the surface roughness $Ra_4$ of the outer surface 61 of the objective resin film 6 and not particularly limited.

<2> Next, if required, the upper surface (the surface to serve as the inner surface 62 of the resin film 6) of the sheet 600 is subjected to a surface roughening.

Accordingly, the surface roughness (a center line mean roughness defined in JIS B 0601: Ra) of the upper surface 602 of the sheet 600 is adjusted, so that the adhesiveness of the resin film 6 to the outer surface of the gasket body 5 can be increased.

The degree of adjusting the surface roughness (Ra) can be represented by variations in the coefficient of kinetic friction before and after the surface roughening on the upper surface 602 of the sheet 600. That is, when the coefficient of kinetic friction (against a sapphire needle) before the surface roughening on the upper surface 602 is defined as $D_1$ and the coefficient of kinetic friction (against a sapphire needle) after the surface roughening is defined as $D_2$, although not specifically limited, a ratio of these coefficient of kinetic frictions $F=D_2/D_1$ satisfies, for example, preferably the relation of approximately $F \geq 2$, more preferably the relation of approximately 2.5 to 8.0. When the ratio of the coefficient of kinetic frictions F satisfies the above range, the adhesiveness of the resin film 6 to the outer surface of the gasket body 5 is improved more.

A method of the surface roughening may include an etching process such as an etching process using sodium compound or sputter etching process; a sand blasting process; a shot blasting process or the like. Among them, the etching process is preferably used as a method of the surface roughening.

According to the etching process, an operation is extremely easy without requiring a major facility, which is advantageous in a shortening of the manufacturing time and a reduction in the manufacturing costs of the gasket.

<3> Next, the gasket 3 is molded using a molding die 100 shown in FIG. 2 and FIG. 3.

The molding die 100 includes a female die (a lower die) 200 and a male die (an upper die) 300. The male die 300 is placed such that it is movable in the vertical direction with respect to the female die 200 in FIG. 2 and FIG. 3.

In addition, the female die 200 and the male die 300 are connected to heaters (not shown) for heating them, respectively.

In the female die 200, a recessed portion 210 is formed so as to be recessed inwardly. The recessed portion 210 is formed so as to be corresponded to the shape of the gasket 3.

On the other hand, on the lower surface of the male die 300, a protruded portion 310 for forming an impacting part 31 of the gasket 3 is formed.

At first, prior to mold the gasket 3, the molding die 100 is heated in advance. The temperature is preferably about 140 to 180° C., for example.

Next, the sheet 600 is placed on the upper surface of the lower die 200 so as to stop up the recessed portion 210. Subsequently, the mixture (compound) 500 of the gasket body material in block form is placed on the upper surface 602 of the sheet 600.

The mixture 500 can be prepared from the gasket body material adjusted at a predetermined blending ratio by using, for example, a sealed kneading machine, an open-roll kneading machine, or the like.

The dimensions of the mixture 500 may be defined, for example, as follows. That is, the volume thereof is preferably almost 1.2 to 3.0 folds of the volume of the gasket body 5, the height (thickness) thereof is preferably almost not less than the depth of the recessed portion 210 (the length in the vertical direction in FIG. 2 and FIG. 3), and the lateral cross-section area (the maximum cross-section area) thereof is preferably almost 1 to 2 folds of the opening area of the recessed portion 210.

Furthermore, the shape of the mixture 500 is not limited to one shown in the figure, and any shape such as a plate, ball, cubic, polygon such as rectangular parallelepiped, or triangular pyramid may be allowable as far as it is formed so as to be easily filled in the recessed portion 210.

In the state of placing the mixture 500 on the upper surface 602 of the sheet 600, when the male die 300 is moved downwardly by operating an operating lever (or a handle) not shown in the figure, the tip end of the protruded portion 310 is brought into contact with the upper surface of the mixture 500 and subsequently the lower surface of the male die 300 is brought into contact therewith to press against the mixture 500 and the sheet 600 downwardly in FIG. 2. At this time, the mixture 500 previously heated and the sheet 600 are in their softened states or in the states close to these states, respectively, so that they are gradually pressed into the recessed portion 210 of the female die 200 by pressing with the male die 300.

Furthermore, the male die 300 is moved downwardly so as to be close to the female die 200, and is heated and pressurized as in the state shown in FIG. 3 to obtain the molded product of the gasket 3.

Consequently, the outer surface of the gasket body 5 is covered with the resin film 6. At this time, the resin film 6 is adhered on the outer surface of the gasket body 5 such that the gasket body material enters into a plurality of minute recessed portions in the inner surface 62 of the resin film 6.

Therefore, in this kind of gasket 3, at the time of sliding in the outer tube 2, especially even in the vicinity of the protruded portions 32 which is a region to be easily peeled off due to the concentration of stress, the resin film 6 can be reliably prevented from being peeled off of the gasket body 5.

For instance, although not specifically limited, the molding conditions can be defined as follows. That is, the temperature is preferably about 140 to 180° C., more preferably about 150 to 170° C., pressure is preferably about 0.5 to 25 MPa, more preferably about 1 to 20 MPa, and the time is preferably about 1 to 20 minutes, more preferably about 5 to 10 minutes.

The material that forms the gasket body material and is capable of obtaining its elasticity by vulcanization is vulcanized by heating and pressurizing in this step.

Furthermore, at this time, the sheet 600 adheres on the outer surface of the gasket body 5 while extending. The degree of extension of the sheet 600 can be, for example, represented by variations in the average thickness between the sheet 600 and the resin film 6, variations in the surface roughness (a center line mean roughness defined in JIS B 0601: Ra) between the lower surface 601 of the sheet 600 and the outer surface 61 of the resin film 6, or the like.

Furthermore, when the surface roughness of the lower surface 601 of the sheet 600 is defined as $Ra_3$ and the surface roughness of the outer surface 61 of the resin film 6 is defined as $Ra_4$, it is preferable that $Ra_4/Ra_3$ satisfies the relation of about 0.25 to 0.9, more preferably satisfies the relation of about 0.5 to 0.8.

When the variation of the surface roughness (Ra) is too small, i.e., the degree of extension of the sheet 600 is small, there may be a case in which it is difficult for the gasket 3 to be manufactured at a high dimensional accuracy. On the other hand, when the variation of the surface roughness (Ra) is too large, i.e., the degree of extension of the sheet 600 is large, the thickness of the resin film 6 may become uneven, which leads to a case of causing a region with a weak strength.

As described above, in this step, the average thickness $T_2$ of the resin film 6 and the surface roughness $Ra_4$ of the outer surface 61 are adjusted.

Note that, in addition to the adjustment with the extension of the sheet 600, the surface roughness $Ra_4$ of the outer surface 61 can be also adjusted, for example, using one obtained by subjecting the inner surface 211 of the recessed portion 210 of the female die 200 to a high-precision processing (e.g., grinding).

<4> Next, when the temperature of the molded product of the gasket 3 is decreased to a predetermined temperature by stopping the heating of the molding die 100, the male die 300 is moved upwardly in FIG. 3 to separate it from the female die 200. Accordingly, the molding die 100 is separated, and the molded product of the gasket 3 is pulled out of the molding die 100.

Subsequently, it is cooled to almost room temperature typically for 0.5 to 3 hours depending on the size of the molded product of the gasket 3.

After that, the undesired portions are cut and removed from the molded product of the gasket 3 using a trimming die to obtain the finished product of the gasket 3.

In the above description, the method of manufacturing a gasket of the present invention has been described with respect to the embodiment illustrated in the figures.

However, the present invention is not limited to this.

EXAMPLES

Hereinafter, there are described concrete examples of the present invention.

At first, an example of a gasket of the present invention will be described.

Example 1

First of all, a gasket was manufactured as follows.

[Manufacture of gasket]

(1) A sheet having predetermined dimensions and predetermined surface roughness formed of polytetrafluoroethylene (a resin film material) manufactured by a skiving processing was prepared.

(2) A 1N-sodium naphthalenide THF solution was applied on the surface of the sheet manufactured in the above step (1), which is to serve as a surface on the gasket body side (the surface to serve as the inner surface of a resin film), followed by washing with distilled water. This operation (etching process using sodium compound) was repeatedly performed to adjust the surface roughness $Ra_2$.

(3) Then, a mixture of the above sheet and styrene butadiene rubber (gasket body material) was placed in a molding die previously heated at 160° C.

(4) Subsequently, the molded product of the gasket was obtained by molding at a die temperature of 160° C. and a mold-clamping pressure of 10 MPa, and for a processing time of 8 minutes.

(5) The molded product of the gasket obtained in the above (4) was pulled out of the molding die and was then cooled at room temperature for 60 minutes, followed by drawing and separating out using a trimming die to obtain the finished product of the gasket.

[Assemble of Syringe]

The gasket obtained by the steps described above was washed with distilled water and then examined, thereafter assembled together with an outer tube and a plunger independently manufactured. Then, the syringe having a structure of FIG. 1 was manufactured. The specifications of the syringe are as follows.

1. Outer Tube

Materials of the outer tube: Copolymer of ethylene and tetracyclo[$4.4.0.1^{2.5}.0.1^{7.10}$]-3-dodecene (cyclic polyolefin).

Inner diameter: 6.3 mm

Length of inner cavity in the longitudinal direction: 54 mm

2. Plunger

Material of plunger: polypropylene

3. Gasket

Surface roughness $Ra_1$ of the outer surface of resin film: 0.3 μm

Coefficient of kinetic friction (against a sapphire needle) of the outer surface of resin film: 0.15

Surface roughness $Ra_2$ of the inner surface of resin film: 4.8 μm

Average thickness T of resin film: 50 μm

Maximum outer diameter: 6.5 mm

Example 2

A gasket was manufactured in the same way as that of the Example 1 except that the surface roughness $Ra_1$ of the outer surface of the resin film was 0.1 μm, and then a syringe was assembled.

At this time, the coefficient of kinetic friction of the outer surface of the resin film (against a sapphire needle) was 0.21.

Note that the surface roughness $Ra_1$ of the outer surface of the resin film used was adjusted by the manufacture using a sheet having the same dimensions and surface roughness as those of the Example 1 described above and also using a molding die where the inside thereof was precisely ground.

Example 3

A gasket was manufactured in the same way as that of the Example 1 except that the surface roughness $Ra_1$ of the outer surface of the resin film was 0.1 μm and that the surface roughness $Ra_2$ of the inner surface of the resin film was 1.7 μm, and then a syringe was assembled.

At this time, the coefficient of kinetic friction of the outer surface of the resin film (against a sapphire needle) was 0.08.

In addition, the surface roughness $Ra_1$ of the outer surface of the resin film was adjusted by using a sheet having the surface roughness different from that of the Example 1 described above. Furthermore, the surface roughness $Ra_2$ of the inner surface of the resin film was adjusted with the concentration of a processing solution and the number of processes of the etching process using sodium compound.

Example 4

A gasket was manufactured in the same way as that of the Example 1 except that the average thickness T of the resin film was 10 μm, and then a syringe was assembled.

Note that the average thickness T of the resin film was adjusted by using a sheet having the thickness (dimension) different from the Example 1 described above.

Example 5

A gasket was manufactured in the same way as that of the Example 1 except that the surface roughness $Ra_1$ of the outer surface of the resin film was 0.5 μm, that the surface roughness $Ra_2$ of the inner surface of the resin film was 8.8 μm, and that the average thickness T of the resin film was 120 μm, and then a syringe was assembled.

At this time, the coefficient of kinetic friction of the outer surface of the resin film (against a sapphire needle) was 0.11.

Note that the surface roughness $Ra_1$ of the outer surface of the resin film and the average thickness T were adjusted by using a sheet having the surface roughness and the thickness (dimension) different from the Example 1 described above. Further, the surface roughness $Ra_2$ of the inner surface of the resin film was adjusted with the concentration of a processing solution and the number of processes of the etching process using sodium compound.

Comparative Example 1

A gasket was manufactured in the same way as that of the Example 1 except that the surface roughness $Ra_2$ of the inner surface of the resin film was 0.3 μm, and then a syringe was assembled.

Note that the surface roughness $Ra_2$ of the inner surface of the resin film was adjusted by omitting the etching process using sodium compound.

Comparative Example 2

A gasket was manufactured in the same way as that of the Example 1 except that the outer surface of the gasket body was not covered with the resin film, and then a syringe was assembled.

Note that the surface roughness of the gasket was 0.3 μm and the coefficient of kinetic friction (against a sapphire needle) was 1.2.

<Evaluations>

For each gasket manufactured in Examples 1 to 5 and Comparative Examples 1 and 2, each of the evaluation tests of the following evaluations 1 to 4 was conducted.

Evaluation 1: Confirmation of Number of Pinholes Generated

The number of pinholes generated at the time of manufacturing each of the gaskets (n=50) in Examples 1 to 5 and Comparative Example 1 was confirmed.

The number (the average number) of pinholes generated in each gasket was evaluated according to the following four stages of criteria.

⊚: Number (average number) of pinholes generated was zero.

○: Number (average number) of pinholes generated was less than one.

Δ: Number (average number) of pinholes generated was one or more and less than ten.

×: Number (average number) of pinholes generated was ten or more.

Evaluation 2: Slidability Test

Each of the syringes (n=50) of Examples 1 to 5 and Comparative Examples 1 and 2 was prepared.

1 mL of distilled water was contained in the containment space of each syringe and a plunger was made to slide at a speed of 500 mm/minute toward the tip end of an outer tube to discharge the distilled water from the containment space.

Then, the sliding resistances of the gaskets to the outer tubes were measured, and the average value thereof was obtained.

The sliding resistance (the average value) of each gasket was evaluated according to the following four stages of criteria.

⊚: Sliding resistance (average value) was less than 500 g.

○: Sliding resistance (average value) was 500 g or more and less than 1000 g.

Δ: Sliding resistance (average value) was 1000 g or more and less than 1500 g.

×: Sliding resistance (average value) was 1500 g or more.

Evaluation 3: Sealability Test 1 mL of distilled water was contained in the containment space of each syringe of Examples 1 to 5 and Comparative Examples 1 and 2, and a plunger was made to slide at a speed of 500 mm/minute toward the tip end of an outer tube to discharge the distilled water from the containment space.

This operation was repeated 100 times for each syringe and a visual observation was performed to confirm the number of times the operation was repeated until the distilled water leaked out from the containment space to the base end side of the outer tube through the gasket.

The sealability of each gasket was evaluated according to the following four stages of criteria.

⊚: No leakage of distilled water even after repeating the operation 100 times.

○: Leakage of distilled water found between the 70th and 99th operations.

Δ: Leakage of distilled water found between the 30th and 69th operations.

×: Leakage of distilled water found anywhere within 30 operations.

Evaluation 4: Peeling Test of Resin Film 1 mL of the air was contained in the containment space of each syringe of Examples 1 to 5 and Comparative Example 1, and a plunger was made to slide at a speed of 500 mm/minute toward the tip end of an outer tube to discharge the air from the containment space.

This operation was repeated 100 times for each syringe and a visual observation was performed to confirm the number of times the operation was repeated until the resin film was peeled off of the gasket body.

The peeling of the resin film in each gasket was evaluated according to the following four stages of criteria.

⊚: No peeling of the resin film even after repeating the operation 100 times.

○: Peeling of the resin film found between the 70th and 99th operations.

Δ: Peeling of the resin film found between the 30th and 69th operations.

×: Peeling of the resin film found anywhere within 30 operations.

The results of Evaluation 1, Evaluation 2, Evaluation 3, and Evaluation 4 are shown in Table 1 shown below, respectively.

TABLE 1

|  | Resin film | | | | | | | | | |
|---|---|---|---|---|---|---|---|---|---|---|
|  | Outer surface | | | | | | | | | |
|  | Surface roughness $Ra_1$ [μm] | Coefficient of kinetic friction (against a sapphire needle) | Inner surface Surface roughness $Ra_2$ [μm] | Average thickness T[μm] | $Ra_2/Ra_1$ | $Ra_2/T$ | Result of confirming number of pinholes generated | Result of slidability test | Result of sealability test | Result of peeling test |
| Example 1 | 0.3 | 0.15 | 4.8 | 50 | 16 | 0.096 | ⊚ | ⊚ | ⊚ | ⊚ |
| Example 2 | 0.1 | 0.21 | 4.8 | 50 | 48 | 0.096 | ⊚ | ○ | ⊚ | ⊚ |
| Example 3 | 1.0 | 0.08 | 1.7 | 50 | 1.7 | 0.034 | ⊚ | ⊚ | ○ | ○ |
| Example 4 | 0.3 | 0.15 | 4.8 | 10 | 16 | 0.48 | ○ | ⊚ | ⊚ | ○ |
| Example 5 | 0.5 | 0.11 | 8.8 | 120 | 17.6 | 0.073 | ⊚ | ⊚ | ○ | ⊚ |
| Comparative Example 1 | 0.3 | 0.15 | 0.3 | 50 | 1 | 0.006 | ⊚ | ⊚ | ⊚ | × |
| Comparative Example 2 | 0.3 | Gasket body (not covered with the resin film) 1.2 | | None | | | no test | × | ⊚ | no test |

As shown in Table 1, it became clear that each of the gaskets (Examples 1 to 5) of the present invention had a small sliding resistance and also a high sealability, and in addition, the generation of pinholes and the peeling of the resin film from the gasket body were prevented.

Particularly, with the gasket (Example 1) of the present invention, in which the surface roughness $Ra_1$ of the outer surface of the resin film was 0.25 to 0.8 μm, the coefficient of kinetic friction (against a sapphire needle) was 0.1 to 0.2, the inner surface of the resin film satisfied the relation of 3.0 $Ra_1 < Ra_2$ and $Ra_2 < 0.1T$, and the average thickness T of the resin film was 15 to 110 μm, the generation of pinholes was prevented more properly, the slidability and the sealability were more excellent, and also the resin film was prevented from being peeled off the gasket body more properly.

On the contrary, each of the gaskets of Comparative Examples 1 and 2 was unsuitable as a gasket. That is, the gasket of Comparative Example 1 had a poor adhesiveness between the gasket body and the resin film, and the resin film was easily peeled off the gasket body. In addition, the gasket of Comparative 2 had an extremely large sliding resistance and was difficult to be used as a gasket.

Next, example of a method of manufacturing the gasket of the present invention will be described.

Example 6

First of all, a gasket was manufactured as follows.

[Manufacture of Gasket]

(1) A sheet formed of polytetrafluoroethylene (a resin film material) manufactured by a skiving processing was prepared. This process is conducted as follows.

At first, powder of polytetrafluoroethylene was filled in a baking molding die and was then compressed at 0 to 30° C. under a pressure of 200 kg/cm$^2$ to obtain a preformed product.

Next, this preformed product was baked for 10 hours at 370° C., followed by cooling under normal pressure to obtain the cylindrical primary molded product.

Subsequently, the primary molded product was placed in a lathe turning machine, kept at a rotational frequency of 35 rpm, and was then subjected to cutting by a cutting blade pressed against the primary molded product at an angle of 40° to obtain a sheet.

Note that the obtained sheet had an average thickness $T_1$ of 70 μm and a surface roughness $Ra_3$ of 0.4 μm.

(2) A liquid ammonia solution of metallic sodium was applied on the upper surface (the surface to serve as the inner surface of a resin film) of the sheet manufactured in the above step (1), followed by washing with distilled water. This operation (etching process using sodium compound) was repeatedly performed.

Note that the upper surface of the sheet had a coefficient of kinetic friction (against a sapphire needle) before etching process using sodium compound (surface roughening) $D_1$ of 0.17, a coefficient of kinetic friction (against a sapphire needle) after etching process using sodium compound $D_2$ of 0.63, and a coefficient of kinetic friction ratio $F=D_2/D_1$ of 3.7.

(3) Then, a mixture of the above sheet and styrene butadiene rubber (gasket body material) was placed in a molding die previously heated at 160° C.

(4) Subsequently, the molded product of the gasket was obtained by molding at a temperature of 160° C. and a pressure of 10 MPa, and for 8 minutes.

(5) After stopping the heating of the molding die, the molding die was separated. From the inside thereof, the molded product of the gasket was pulled out and was then left for 1 hour to cool it down to room temperature.

Then, undesired portions were isolated from the molded product of the gasket using a trimming die to obtain the finished product of the gasket.

[Assemble of Syringe]

The gasket obtained by the steps described above was washed with distilled water, and examined, thereafter assembled together with an outer tube and a plunger independently manufactured. Then, the syringe having a structure of FIG. 1 was manufactured. The specifications of the syringe are as follows.

1. Outer Tube

Materials of the outer tube: Copolymer of ethylene and tetracyclo[4.4.0.1$^{2.5}$.1$^{7.10}$]-3-dodecene (cyclic polyolefin).

Inner diameter: 6.3 mm

Length of inner cavity in the longitudinal direction: 54 mm

2. Plunger

Material of plunger: polypropylene

3. Gasket

Surface roughness $Ra_4$ of the outer surface of resin film: 0.3 μm ($Ra_4/Ra_3=0.75$)

Coefficient of kinetic friction (against a sapphire needle) of the outer surface of resin film: 0.15

Average thickness $T_2$ of resin film: 50 μm

Maximum outer diameter: 6.5 mm

Example 7

A gasket was manufactured and a syringe was assembled by the same ways as those of Example 6 described above except that the coefficient of kinetic friction ratio $F=D_2/D_1$ of the upper surface of the sheet was defined as 2.

In addition, the upper surface of the sheet had a coefficient of kinetic friction (against a sapphire needle) before an etching process using sodium compound (surface roughening) $D_1$ of 0.17 and a coefficient of kinetic friction (against a sapphire needle) after the etching process using sodium compound $D_2$ Of 0.34.

Comparative Example 6

The following gasket was manufactured and a syringe was assembled by the same ways as those of Example 6 described above except that a sheet (4 μm in average thickness $T_1$ and 0.25 μm in surface roughness $Ra_3$) manufactured by a casting method was used and etching process using sodium compound on the upper surface of the sheet was omitted.

3. Gasket

Surface roughness $Ra_4$ of the outer surface of resin film: 0.05 μm ($Ra_4/Ra_3=0.2$)

Coefficient of kinetic friction (against a sapphire needle) of the outer surface of resin film: 0.4

Average thickness $T_2$ of resin film: 0.7 μm

Maximum outer diameter: 6.5 mm

Note that the gasket of Comparative Example 6 come at a high manufacturing cost and also required a long manufacturing time compared with the gaskets of Examples 6 and 7.

Comparative Example 7

A gasket was manufactured in the same way as that of the Example 6 except that the outer surface of the gasket body was not covered with the resin film, and then a syringe was assembled.

Note that the surface roughness of the gasket was 0.3 μm, and the coefficient of kinetic friction (against a sapphire needle) was 1.2.

<Evaluations>

For each gasket manufactured in Examples 6 and 7 and Comparative Examples 6 and 7, each of evaluation tests of the following evaluations 1 to 4 was conducted.

Evaluation 1: Confirmation of the Number of Pinholes Generated

The number of pinholes generated at the time of manufacturing each of the gaskets (n=50) in Examples 6 and 7 and Comparative Example 6 was confirmed.

For the number (the average number) of pinholes generated in each gasket was evaluated according to the following four stages of criteria.

⊚: Number (average number) of pinholes generated was zero.

○: Number (average number) of pinholes generated was less than one.

Δ: Number (average number) of pinholes generated was one or more and less than ten.

×: Number (average number) of pinholes generated was ten or more.

Evaluation 2: Slidability Test

Each of syringes (n=50) of Examples 6 and 7 and Comparative Examples 6 and 7 was prepared. 1 mL of distilled water was contained in the containment space of each syringe and a plunger was made to slide at a speed of 500 mm/minute toward the tip end of an outer tube to discharge the distilled water from the containment space.

Then, the sliding resistances of the gaskets at this time against the outer tubes were measured, and the average value thereof was obtained.

The sliding resistance (the average value) of each gasket was evaluated according to the following four stages of criteria.

⊚: Sliding resistance (average value) less than 500 g.

○: Sliding resistance (average value) 500 g or more and less than 1000 g.

Δ: Sliding resistance (average value) 1000 g or more and less than 1500 g.

×: Sliding resistance (average value) 1500 g or more.

Evaluation 3: Sealability Test 1 mL of distilled water was contained in the containment space of each syringe in Examples 6 and 7 and Comparative Examples 6 and 7 and a plunger was made to slide at a speed of 1500 mm/minute toward the tip end of an outer tube to discharge the distilled water from the containment space.

This operation was repeated 100 times for each syringe and a visual observation was performed to confirm the number of times the operation was repeated until the distilled water leaked out from the containment space to the base end side of the outer tube through the gasket.

The sealability of each gasket was evaluated according to the following four stages of criteria.

⊚: No leakage of distilled water even after repeating the operation 100 times.

○: Leakage of distilled water found between the 70th and 99th operations.

Δ: Leakage of distilled water found between the 30th and 69th operations.

×: Leakage of distilled water found anywhere within 30 operations.

Evaluation 4: Peeling Test of Resin Film 1 mL of the air was contained in the containment space of each syringe in Examples 6 and 7 and Comparative Examples 6 and 7 and a plunger was made to slide at a speed of 500 mm/minute toward the tip end of an outer tube to discharge the air from the containment space.

This operation was repeated 100 times for each syringe and a visual observation was performed to confirm the number of times the operation was repeated until the resin film was peeled off of the gasket body.

The peeling of the resin film in each gasket was evaluated according to the following four stages of criteria.

⊚: No peeling of the resin film after repeating the operation 100 times.

○: Peeling of the resin film found between the 70th and 99th operations.

Δ: Peeling of the resin film found between the 30th and 69th operations.

×: Peeling of the resin film found within 30 operations.

The results of Evaluation 1, Evaluation 2, Evaluation 3, and Evaluation 4 are shown in Table 2 below, respectively.

TABLE 2

| | Method of manufacturing sheet | Result of confirming number of pinholes generated | Result of slidability test | Result of sealability test | Result of peeling test |
|---|---|---|---|---|---|
| Example 6 | Skiving | ⊚ | ⊚ | ⊚ | ⊚ |
| Example 7 | processing | ⊚ | ⊚ | ⊚ | ○ |
| Comparative Example 6 | Casting method | × | Δ | ⊚ | Δ* |
| Comparative Example 7 | Gasket body not covered with the resin film | No test | × | ⊚ | No test |

*Partial peeling around pinholes

As shown in FIG. 2, it became evident that each of the gaskets (Examples 6 and 7) of the present invention had no generation of any pinhole at the time of molding, a small sliding resistance, and a high sealability. In addition, the resin film was hardly peeled off the gasket body.

In particular, in the gasket (Example 6) of the present invention, in which the surface of the sheet to serve as an inner surface of the resin film was subjected to surface roughening in advance to molding, and the dynamic friction ratio F before and after the surface roughening satisfied the relation of 2.5 to 8.0, the resin film was prevented from being peeled off the gasket body more properly.

On the contrary, each of the gaskets of Comparative Examples 6 and 7 was unsuitable as a gasket. That is, in the gasket of Comparative Example 6 pinholes were generated at the time of molding and the gasket showed a large sliding resistance, and the resin film was easily peeled off the gasket body. Furthermore, the gasket of Comparative Example 2 had an extremely large sliding resistance, so that it was hard to be used as a gasket.

INDUSTRIAL APPLICABILITY

As described above, in the gasket of the present invention, the surface roughness of the surface of the resin film on the gasket body side and the surface roughness of the surface of the resin film on the outer tube side are properly defined, so that a high slidability and a high sealability can be obtained while preventing the resin film from being peeled off the gasket body.

In addition, by selecting the average thickness of the resin film, a molding defect such as pinholes is prevented, sealability of the gasket is improved and so forth.

Further, the gasket of the present invention has an excellent slidability, so that it is possible to omit the applications of lubricant on the outer surface (the outer periphery) of the gasket and on the inner peripheral surface of the outer tube. Therefore, for example, when a drug solution or the like is contained in the outer tube, a decrease in the activities and concentrations of medicinal ingredients in the drug solution can be prevented.

Furthermore, according to the method of manufacturing a gasket of the present invention, it is possible to manufacture a gasket, in which the generation of a molding defect such as pinholes can be prevented, by simple manufacturing steps.

Particularly, by using the resin film manufactured by skiving processing, the resin film can be provided as one having a relative large thickness to obtain a sufficient strength. Therefore, a molding defect as described above can be prevented properly.

Also, the gasket body material is formed of a material which is able to obtain its elasticity with vulcanization, so that vulcanization can be conducted by heating and pressurizing at the time of molding the gasket. Therefore, the additional step of vulcanization of the gasket body material can be omitted so that it is advantageous in reducing the manufacturing costs and in shortening the manufacturing time.

Further, the adhesiveness of the resin film to the gasket body can be improved by subjecting the surface of the resin film on the gasket body side to surface roughening in advance to the molding of the gasket.

Furthermore, a gasket having a high slidability can be manufactured when the resin film is formed of a material having a smaller coefficient of friction than the gasket body material. Therefore, the application of lubricant to the outer surface (outer periphery) of the gasket can be omitted.

Additionally, the sealability of the gasket can be improved by adjusting the surface roughness (Ra) of the surface of the resin film on the side opposite to the gasket body.

What is claimed is:

1. A gasket installed slidably in an outer tube of a syringe, including a gasket body and a resin film formed of a material lower in coefficient of friction than a material of the gasket body, which covers at least an outer periphery of the gasket body, in which when a surface roughness of the resin film on the outer tube side is defined as $Ra_1$ and a surface roughness of the resin film on the gasket body side is defined as $Ra_2$, a relationship of $1.5\, Ra_1 \leq Ra_2$ is satisfied.

2. The gasket according to claim 1, in which the surface roughness $Ra_1$ is 0.1 to 1.5 μm.

3. The gasket according to claim 1, in which $Ra_2 < 0.5T$ when an average thickness of the resin film is defined as T.

4. The gasket according to claim 3, in which the average thickness Y of the resin film is 1 to 200 μm.

5. The gasket according to claim 1, in which the surface of the resin film on the outer tube side has a coefficient of kinetic friction (against a sapphire needle) of 0.3 or less.

6. The gasket according to claim 1, in which the resin film is formed of a fluorocarbon resin.

7. The gasket according to claim 1, in which the surface roughness $Ra_2$ is adjusted by subjecting the surface of the resin film on the gasket body side to a surface roughening.

8. The gasket according to claim 7, in which the surface roughening is performed by using an etching process.

9. The gasket according to claim 1, in which the gasket body and the resin film are put into close contact with each other such that the gasket material enters into a plurality of minute recessed portions of the surface of the resin film on the gasket body side.

10. The gasket according to claim 1, in which the gasket body is formed of an elastic material.

* * * * *

UNITED STATES PATENT AND TRADEMARK OFFICE
CERTIFICATE OF CORRECTION

PATENT NO. : 7,111,848 B2
APPLICATION NO. : 10/380518
DATED : September 26, 2006
INVENTOR(S) : Kouichi Tachikawa et al.

It is certified that error appears in the above-identified patent and that said Letters Patent is hereby corrected as shown below:

Claim 4, Column 22, Line 15: change "Y" to --T--.

Signed and Sealed this

Twenty-ninth Day of May, 2007

JON W. DUDAS
*Director of the United States Patent and Trademark Office*